(12) United States Patent
Dawson et al.

(10) Patent No.: US 6,541,199 B1
(45) Date of Patent: *Apr. 1, 2003

(54) IDENTIFICATION OF A NEW EHRLICHIA SPECIES FROM A PATIENT SUFFERING FROM EHRLICHIOSIS

(75) Inventors: Jacqueline E. Dawson, Atlanta; Burt Anderson, Tucker, both of GA (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/061,770

(22) Filed: Apr. 16, 1998

Related U.S. Application Data

(62) Division of application No. 08/943,464, filed on Oct. 3, 1997, now Pat. No. 5,789,176, which is a continuation of application No. 08/394,464, filed on Feb. 27, 1995, now abandoned, which is a division of application No. 08/147, 891, filed on Nov. 5, 1993, now Pat. No. 5,413,931, which is a continuation of application No. 07/687,526, filed on Apr. 18, 1991, now abandoned.

(51) Int. Cl.$^7$ .............................. C12Q 1/68; C12N 1/00; C12N 1/12; C12N 1/04; C07H 21/04
(52) U.S. Cl. ..................... 435/6; 435/243; 435/252.1; 435/260; 536/23.7; 536/24.32; 536/24.33
(58) Field of Search .............................. 435/240.2, 243, 435/252.1, 260, 6; 536/23.7, 24.32, 24.33

(56) References Cited

U.S. PATENT DOCUMENTS 5,413,931 A 6/1995 Dawson et al.

Primary Examiner—James C. Housel
Assistant Examiner—Rodney P. Swartz
(74) Attorney, Agent, or Firm—Klarquist Sparkman, LLP

(57) ABSTRACT

A new isolate of Ehrlichia species has been obtained from a patient suffering from ehrlichiosis. The new isolate has been found to be similar, but distinctly different from *E. canis*. A diagnostic kit and methods for diagnosing ehrlichiosis in humans and for screening drugs toxic to the new isolate have been described.

2 Claims, 2 Drawing Sheets

Fig. 2

```
  1 ACGCTGTAAA CGATGAGTGC TAAATGTGAG GATTTTATCT TTGTATTGTA GCTAACGCGT  60
  1 ACGCTGTAAA CGATGAGTGC TAAATGTGAG GATTTTATCT TTGTATTGTA GCTAACGCGT  60

61 TAAGCACTCC GCCTCCCCAC TCAGGTCGCA AGACTAAAAC TCAAAGGAAT TGACGGGGAC 120
 61 TAAGCACTCC GCCTCCCCAC TCAGGTCGCA AGACTAAAAC TCAAAGGAAT TGACGGGGAC 120

121 CCGCACAAGG CTGGAGCATG TGGTTTAATT CGATGCAACG CGAAAAACCT TACCACTTTT 180
121 CCGCACAAGG CTGGAGCATG TGGTTTAATT CGATGCtACG CGAAAAACCT TACCACTTTT 180

181 TGACATGAAG GTCGTATCCC TCCTAATAGG GGGAGTCAGT TCGGCTGGAC CTTACACAGG 240
181 TGACATGAAG GTCGTATCCC TCCTAAcAGG GGGAGTCAGT TCGGCTGGAC CTTACACAGG 240

241 TGCTGCATGG CTGTCGTCAG CTCGTGTCGT GAGATGTTGG GTTAAGTCCC GCAACGAGCG 300
241 TGCTGCATGG tTGTCGTCAG CTCGTGTCGT GAGATGTTGG GTTAAGTCCC GCAACGAGCG 300

301 CAACCCTCAT CCTTAGTTAC CAACAGGTAA TGCTGGGCAC TCTAAGGAAA CTGCCAGTGA 360
301 CAACCCTCAT tCTTAGTTAC CAACAGGTAA TGCTGGGCAC TCTAAGGAAA CTGCCAGTGA 360

361 TAAACTGGAG GAAGGTCCCC ATGATGTCAA GTCAGCACGG CCCTTATAAG GTGGGCTACA 420
361 TAAACTGGAG GAAGGTCCCC ATGATGTCAA aTCAGCACGG CCCTTATAgG GTGGGCTACA 420

421 CACGTGCTAC AATGGCAACT ACAATAGGTC GCGAGACCGC AAGGTTTAGC TAATCCATAA 480
421 CACGTGCTAC AATGGCAACT ACAATAGGTt GCGAGACCGC AAGGTTTAGC TAATCCATAA 480

481 AAGTTGTCTC AGTTCGGATT GTTCTCTGCA ACTCGAGAGC ATGAAGTCGG AATCGCTAGT 540
481 AAGTTGTCTC AGTTCGGATT GTTCTCTGaA ACTCGAGAGC ATGAAGTCGG AATCGCTAGT 540

541 AATCGTGGAT CATCATGCCA CGGTGAATAC GTTCTCGGGT CTTGTACACA CTGCCCGTCA 600
541 AATCGTGGAT CATCAcGCCA CGGTGAATAC GTTCTCGGGT CTTGTACACA CTGCCCGTCA 600

601 CGCCATGGGA ATTGGCTTAA CTCGAAGCTG GTGTGCTAAC CGCAAGGAAG CAGCCATTTA 660
601 CGCCATGGGA ATTGGCTTAA CTCGAAGCTG GTGTGCTAAC CGCAAGGAAG CAGCCATTTA 660

661 AGGTTGGGTT AGTGACTAGG GTG        683
661 AGGTTGGGTT AGTGACTAGG GTG        683
```

TOP: HUMAN EHRLICHIA CHAFFEENSIS AGENT          PERCENT SIMILARITY: 98.682
BOTTOM: *EHRLICHIA CANIS* (OKLAHOMA STRAIN)        PERCENT IDENTITY: 98.682

IDENTIFICATION OF A NEW EHRLICHIA SPECIES FROM A PATIENT SUFFERING FROM EHRLICHIOSIS

This is a division of prior application Ser. No. 08/943,464, now U.S. Pat. No. 5,739,176, filed Oct. 3, 1997, which is a continuation of application Ser. No. 08/394,464, filed Feb. 27, 1995, now abandoned, which is a divisional of application Ser. No. 08/147,891, filed, Nov. 5, 1993, now U.S. Pat. No. 5,413,931, which is a continuation of application Ser. No. 07/687,526, filed Apr. 18, 1991, now abandoned, which are hereby incorporated herein by reference in their entirety.

This invention relates to the identification and characterization of a new microorganism isolated from a patient suffering from ehrlichiosis. The new organism, designated herein as *Ehrlichia chaffeensis*, is similar to but distinct from *Ehrlichia canis*.

BACKGROUND OF THE INVENTION

Human ehrlichiosis is a newly recognized disease characterized by fever, headache, malaise, thrombocytopenia, leukopenia, and elevated liver enzymes (Anon., *M.M.W.R.* 37, 270, 275, 1988; Fishbein, et al., *JAMA* 257, 3100, 1987; Fishbein, et al., *J. Infect. Dis.* 160, 803,1989; Eng, et al., *JAMA* 264, 2251, 1990). Often the patients also have a history of tick exposure. The only Ehrlichia species known to infect humans is *Ehrlichia sennetsu*, the agent responsible for sennetsu rickettsiosis, a disease that has been reported only in Japan and Malaysia (Ristic, in *Microbiology* 1986, L. Leive, Ed., American Society for Microbiology, Washington, D.C., 1986, pp. 182–187). Since recognition of a human form of ehrlichiosis in the United States in 1986, laboratory-based surveillance has led to the identification of about 215 persons with variable antibody titer to *E. canis* in 20 states, predominantly in southeastern and south central areas of the United States (Fishbein, et al., *J. Infect. Dis.*, 160, 803, 1989; Eng, et al., *JAMA* 264, 2251, 1990). It may be noted, however, that despite such serologic evidence, the causative agent of human ehrlichiosis remained unidentified and the etiology of the disease also remained undetermined.

SUMMARY OF THE INVENTION

It is, therefore, an object of the present invention to isolate, identify and characterize the agent associated with human ehrlichiosis, the agent thus isolated having been designated herein as "*Ehrlichia chaffeensis*" or "human Ehrlichia".

It is noted that if the scientific community accepts the change of nomenclature of *E. chaffeensis* to *E. homosapiensis* or other designation, then of course it should be recognized accordingly.

It is another object of the present invention to grow the *Ehrlichia chaffeensis* isolate in a cell culture.

It is also an object of the present invention to provide a recombinant molecule or construct containing *E. chaffeensis* nucleotide sequence or *E. chaffeensis*-specific fragment thereof.

A further object of the present invention is to prepare antibodies having specificity particularly against *E. chaffeensis*.

A still further object of the present invention is to provide cloned genes of *E. chaffeensis* that encode *E. chaffeensis*-specific antigens.

An additional object of the present invention is to provide a composition comprising an immunogenic amount of *E. chaffeensis* antigen, either naturally produced or recombinantly made, to induce antibodies against *E. chaffeensis* in a host susceptible to infection by *E. chaffeensis*.

A further object of the present invention is to provide an immunoassay for detecting human ehrlichiosis employing *E. chaffeensis* or a fragment derived therefrom as an antigen.

Another object of the present invention is to provide a diagnostic kit comprising a container containing *E. chaffeensis*-specific antigen or antibody.

Yet another object of the present invention is to provide a method for screening the toxicity of a drug against *E. chaffeensis* by comparing the growth of *E. chaffeensis* in the presence and absence of the drug in a cell culture environment.

Various other objects and advantages will become evident from the following detailed description of the invention.

BRIEF DESCRIPTION OF DRAWINGS

The above and other objects, features and many of the attendant advantages of the invention will be better understood upon a reading of the following detailed description when considered in connection with the accompanying drawing wherein:

FIG. 2 shows the 16S rRNA nucleotide sequences of *E. chaffeensis* (SEQ ID NO:1) and *E. canis* (SEQ ID NO:2).

DETAILED DESCRIPTION OF INVENTION

Figure 1:
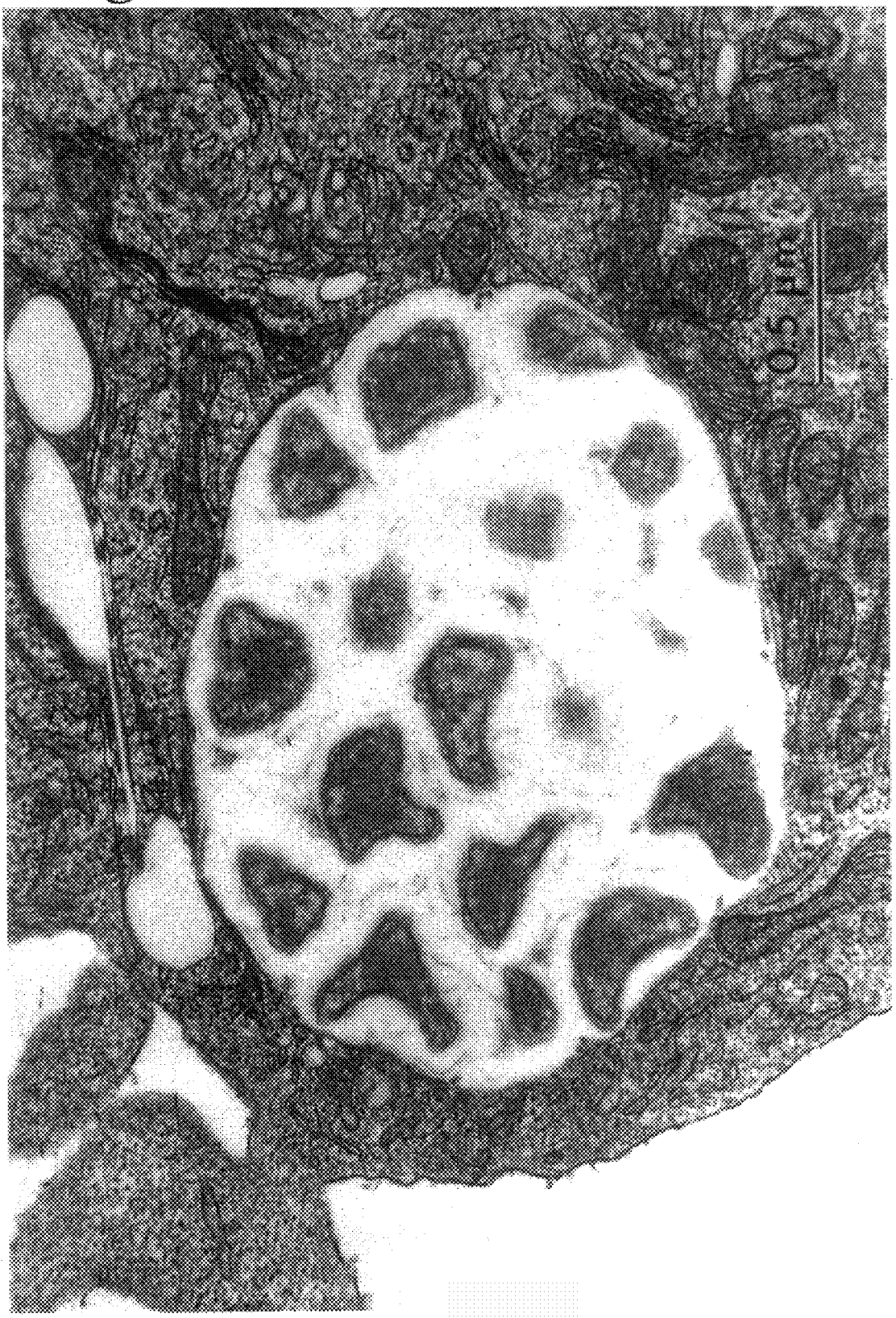
FIG. 1 shows transmission electron micrograph of the human Ehrlichia isolate in the cytoplasm of a DH82 cell. Cell cultures were scraped from flasks and centrifuged at 180×g for 10 minutes. The resulting pellets were fixed at 4° C. in 2.5% 0.2M phosphate buffered glutaraldehyde, post-fixed in 1% buffered osmium tetroxide, dehydrated in a standard ethanol series, and embedded in a modified Araldite-Epon mixture. Sections were stained with uranyl acetate and lead citrate. Organisms are seen in a membrane-bound morulae. Bar=0.5 $\mu$m.

The above and various other objects and advantages of the present invention are achieved by obtaining a biologically pure isolate of *Ehrlichia chaffeensis*, its cloned genes and antigenic products.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

Isolation, Identification and Characterization of *E. chaffeensis*

A 21-year-old man (Table 1, patient no. 1) was admitted to a medical clinic in Arkansas on Jul. 19, 1990 with fever (103° F.), headache, nausea, and vomiting. A physical examination revealed prominent cervical lymphadenopathy, splenomegaly and no rash. Multiple excoriated lesions from constant (11 days) exposure to ticks, chiggers, and mosquitoes were observed. Five days after the onset of illness, hematocrit was 40.1%, the white cell count was 2200 per cubic millimeter, and the platelet count was 100,000 per cubic millimeter.

A small volume of blood (30 ml. heparin and 5 ml. EDTA) was drawn from the patient and shipped with cold packs to the Centers for Disease Control. The leukocytes were separated from the red blood cells (30 ml. heparinized whole blood) approximately 24 hours after collection, and layered onto a previously established monolayer of DH82 (continuous canine macrophage) cells with minimum essential medium supplemented with 1% L-glutamine and 12.5% heat-inactivated fetal bovine serum (Dawson, et al., *J. Infect. Dis.*, 163, 564, 1991). The culture was maintained at 37° C. and monitored by direct immunofluorescence using a fluorescein conjugate prepared from the serum of a patient with ehrlichiosis.

Organisms closely resembling ehrlichieae were first observed in the cytoplasm of cultured macrophages 35 days after the addition of the infected blood (FIG. 1). Thereafter, the proportion of infected macrophages increased, reaching a maximum of 80% on day 48. Uninoculated control cultures of the DH82 cells remained free of organisms.

Electron microscopic examination of the infected cells revealed that inclusion bodies were surrounded by a distinct cytoplasmic membrane (FIG. 1). Each individual organism was surrounded by two membranes, the inner plasma membrane and the outer cell wall. The organisms were also extremely pleomorphic, ranging in shape from oval to boomerang to diamond.

The human isolate thus obtained appears to be antigenically related to the etiologic agent of human ehrlichiosis as suggested by the positive indirect immunofluorescence reactions obtained when serum samples were examined from 12 patients previously diagnosed by the indirect immunofluorescent antibody test, and 2 patients suspected of having ehrlichiosis based on the clinical symptoms (Table 1). Serum specimens from the 14 patients reacted strongly with the newly isolated organism. In two cases (patients no. 1 and 6), a specific fluorescein response was observed only with the human isolate. The negative control sera, from healthy adults, showed no reaction to either organism.

DNA was extracted from the original whole blood sample (EDTA) and utilized as a polymerase chain reaction (PCR) template to produce amplified DNA for cloning and sequencing. DNA was also extracted from the DH82 cell line infected with the new isolate, with *E. canis* Oklahoma isolate as described by Dawson, et al., *J. Infect. Dis.* (163, 564, 1991), and uninfected DH82, for similar amplification and sequence comparison. Samples were amplified for 40 cycles in a thermal cycler using degenerate primers specific for the 3' half of eubacterial 16S ribosomal RNA (rRNA) (Wilson, et al., *J. Clin. Microbiol.* 28, 1942, 1990) and containing unique restriction sites on the 5' ends. PCR products corresponding to the 16S rRNA sequence were seen in all samples except when uninfected DH82 derived DNA was used as a template. The resulting PCR products were cloned into pUC19 and sequenced. All samples were amplified, cloned and sequenced independently 2 times to prevent the reading of Taq polymerase incorporation errors. The PCR product from the patient's blood sample matched the product from the new isolate grown in the DH82 cells for all 683 nucleotides defined within the PCR primers. A comparison with available sequence data also revealed that it was 86.8% related to *E. risticii* (Genbank Accession # M21290), a recently isolated equine pathogen. Serologic data and 16S rRNA sequencing further indicated that the newly isolated Ehrlichia is similar, but not identical to *E. canis*. FIG. 2 shows the comparative nucleotide sequences of the 16S rRNA of *E. canis* and *E. chaffeensis*. The association of the new isolate with human ehrlichiosis further indicates that the new isolate may be involved in the etiology of human ehrlichiosis.

Of course, the availability of the new Ehrlichia isolate of the present invention now makes it possible to prepare a composition comprising an effective amount of *Ehrlichia chaffeensis* antigen to induce an immune response to *Ehrlichia chaffeensis* in a host susceptible to infection by *Ehrlichia chaffeensis*, and a pharmaceutically acceptable carrier. A diagnostic kit in accordance with the present invention comprises at least a container containing an antigen which reacts specifically with anti-*Ehrlichia chaffeensis* antibodies, and instructional material to perform the diagnostic test.

Similarly, a method for diagnosing human ehrlichiosis comprises the step of reacting a sample of the biological fluid (such as blood, serum plasma and the like) or a tissue obtained from an individual suspected of affliction with ehrlichiosis, with an *E. chaffeensis* specific antigen, the occurrence of a positive immunological reaction being indicative of ehrlichiosis in said individual. An example of such a diagnostic test is the indirect fluorescent antibody (IFA) test as described herein above. In order to prepare antigen slides for the IFA test, cells from *E. chaffeensis*-infected DH82 cultures (80–90% infection) were suspended in culture supernatant. This suspension was then either used immediately or lyophilized and when necessary reconstituted in distilled water. One drop (about 3 microliters) of the antigen was then placed onto each well of a teflon-coated slide. The slides were air-dried for about 1 hour and stored at −90° C. As needed, slides were thawed and then fixed in acetone for about 15 minutes. The serum sample was screened at a dilution of 1:64 in phosphate-buffered saline solution. When distinct staining of *E. chaffeensis* organisms was observed at this titer, serial two-fold dilutions were made. Serologic results were recorded as the reciprocal of the highest dilution at which specific fluorescence of *E. chaffeensis* morulae were observed.

For the preparation of *E. chaffeensis* specific antibodies, *Ehrlichia chaffeensis* is grown in the DH82 cell line, or in any other cell line which will support the growth of *E. chaffeensis*, and purified by dounce homogenization followed by low speed centrifugation. Mice are then inoculated with this homogenate or any portion thereof. After approximately 4 weeks, a couple of days before hybridoma formation, the mice are given a booster inoculation. Spleens from primed and boosted mice are then harvested. Hybridomas are produced by fusion with a nonsecretor mouse myeloma cell line (SP2/0) by the method of Kearney et al. (Kearney, et al, 1979, *J. Immunol.* 123:1548–1550). Selected antibody-producing cultures identified by the IFA test or ELISA are expanded in cell culture and stored frozen until cloning. Cells shown by the IFA test or ELISA to be producing antibody to *E. chaffeensis*, are expanded in cell culture from the frozen state and cloned by limiting dilution. The resulting monoclonal antibody-producing cultures are in turn expanded in cell culture. Selected clones are subsequently inoculated into mice for specific antibody production in ascitic fluids. These ascitic fluids are stored frozen until tested. Culture fluids and ascitic fluids are evaluated by IFA, ELISA or any suitable immunoassay.

The availability of *E. chaffeensis* specific antibodies now makes it possible to provide a diagnostic kit for detecting the presence of *E. chaffeensis* or *E. chaffeensis* antigens. Such a kit comprises at least a container containing an antibody which reacts specifically with *E. chaffeensis* antigens and instructional material to perform an immunoassay.

In order to determine the optimal treatment for human ehrlichiosis, the in vitro susceptibility to a candidate drug or a number of commonly used antibiotics is determined. Approximately $10^4$ DH82 cells (at least 50% of these cells are infected with *E. chaffeensis*) are added to each well of a 96 well microtiter plate. After a one hour incubation, the media is replaced with media containing varying concentrations of tetracycline, doxycycline, minocycline, penicillin, erythromycin, gentamicin, rifampin, co-trimoxasole, ciprofloxacin or other drug of interest. The percentage of infected cells is then evaluated by wright giemsa stain and IFA daily for 8 days, the lesser the percentage of infected cells, the greater the toxicity of the drug.

Cloning and Purification of *E. chaffeensis* Antigens

*E. chaffeensis* is grown in the DH82 cell line or in any other cell line which will allow the growth of *E. chaffeensis*, and purified by standard renograffin density gradient centrifugation. The Ehrlichia is then lysed and the DNA extracted via standard procedure using 1.0% SDS and proteinase K. The resulting DNA is then physically size fractionated using sonication and gel purification and linked with EcoRI linkers and cloned into lambda phage vector lambda zapII following standard procedures such as described in Maniatis et al, 1982, Molecular Cloning—A Laboratory Manual, Cold Spring Harbor, N.Y. The recombinant plaques are screened for antigen production via ELISA with primary antibody being human convalescent sera absorbed with an *E. coli* lysate. Antigen expressing clones are subcloned.

Those subclones expressing *E. chaffeensis* specific antigens are sequenced and corresponding synthetic peptides are constructed from the deduced amino acid sequence for use as diagnostic antigens or immunogens. Alternatively, recombinant antigens could be purified by affinity chromatography or High Pressure Liquid Chromatography (HPLC) and the like.

Detection of Ehrlichiosis in Humans

Primers specific for *E. chaffeensis* have been constructed from the 16S rRNA sequence. The sequence of these primers is HE1=5' CAATTGCTTATAACCTTTTGGTTATAAAT 3' (SEQ ID NO:3) and HE3=5'TATAGGTACCGTCA TTATCTTCCCTAT 3'(SEQ ID NO:4). These primers define a 389 base pair product upon amplification and are also useful for amplifying DNA from organisms found in blood from patients with ehrlichiosis using the standard polymerase chain reaction technique. Blood is processed similar to the amplification method used for Rocky Mountain spotted fever diagnosis (Tzianabos et al., *J. Clin. Microbiol.*, 27:3866–2868, 1989.) The resulting DNA is amplified for 40 cycles using a thermal cycler. The correct size PCR-product is considered presumptive evidence of ehrlichiosis. Test results indicate success with 4 out of 5 infected human blood samples which were identified positive and 3 uninfected blood samples which were identified negative. An oligonucleotide probe may then be used to confirm the polymerase chain reaction product as belonging to the genus Ehrlichia. Such a probe sequence may be 5' GCCATTAGAAATGATGGGTAATACTGTATAA 3' (SEQ ID NO:5).

A second method for diagnosis would be to use the whole cell antigen or purified *E. chaffeensis* as an ELISA antigen by solubilizing whole Ehrlichia and attaching to an ELISA plate. Human serum antibodies are then allowed to react with this antigen and secondary anti-human peroxidase-conjugated antibody is then reacted with the antigen-primary antibody complex. The levels of human anti-Ehrlichia antibodies could be quantitated by reacting the complex with a colorimetric substrate for peroxidase or by other suitable method well known to one of ordinary skill in the art.

Deposit

A deposit of the DH82TIED (Human) cells infected with *Ehrlichia chaffeensis* in accordance with the present invention has been made under Budapest Treaty at the ATCC, 10801 University Boulevard, Manassas, Va. 20110-2209 on Jan. 29, 1991 under accession number CRL 10679. The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Indirect fluorescent antibody titers of acute and convalescent sera from 14 patients, tested with *E. canis* and the human Ehrlichia isolate. Starting at a dilution of 1:64, serial twofold dilutions of the acute and convalescent-phase sera were made in 0.15 M PBS solution. Fluorescein-conjugated rabbit antihuman IgG was prepared at the Centers for Desease Control. Serologic results were reported as the reciprocal of the highest dilution at which specific fluorescence of Ehrlichia morulae or individual organisms was observed.

| Patient No. | Tick Exposure State | Days After Onset | E. canis | Human Ehrlichia Isolate |
|---|---|---|---|---|
| 1* | AR | 3 | <64 | <64 |
|  |  | 39 | <64 | 256 |
| 2 | GA | 11 | <64 | <64 |
|  |  | 51 | 128 | 256 |
| 3 | OK | 26 | <64 | <64 |
|  |  | 40 | 512 | 256 |
| 4 | NJ | 7 | 1024 | 1024 |
|  |  | 25 | 512 | 512 |
|  |  | 135 | 256 | 256 |
| 5 | NC | 8 | <64 | <64 |
|  |  | 17 | 4096 | 2048 |
| 6 | SC | 8 | <64 | <64 |
|  |  | 20 | <64 | 2048 |
|  |  | 28 | <64 | 2048 |
| 7 | WY | 10 | 64 | 32 |
|  |  | 24 | 512 | 512 |
| 8 | TX | 16 | 4096 | 4096 |
|  |  | 28 | 1028 | 1028 |
| 9 | MO | 13 | <64 | <64 |
|  |  | 24 | 512 | 1028 |
| 10 | AR | 10 | 512 | 512 |
|  |  | 24 | 16384 | 32768 |
| 11 | TN | −19** | <64 | <64 |
|  |  | 55 | 256 | 256 |
| 12 | VA | 18 | 32768 | 32768 |
|  |  | 38 | 8192 | 8192 |
| 13 | FL | 10 | 1024 | 2048 |
|  |  | 28 | 8192 | 16384 |
| 14 | OK | 8 | <64 | <64 |
|  |  | 21 | 4096 | 16384 |

* = patient from whom Ehrlichia isolate was made
** = specimen obtained 19 days before onset of disease

What is claimed is:

1. A purified antigen purified from and specific for *Ehrlichia chaffeensis*, wherein the antigen comprises a whole purified human *Ehrlichia chaffeensis* organism.

2. A composition comprising an amount of an antigen purified from and specific for *Ehrlichia chaffeensis*, wherein the antigen comprises a whole purified human *Ehrlichia chaffeensis* organism and wherein the antigen is effective to induce an immune response to *Ehrlichia chaffeensis* in a host susceptible to infection by *Ehrlichia chaffeensis*; and a pharmaceutically acceptable carrier.

* * * * *

SEQUENCE LISTING

<160> NUMBER OF SEQ ID NOS: 5

<210> SEQ ID NO 1
<211> LENGTH: 683
<212> TYPE: DNA
<213> ORGANISM: Ehrlichia chaffeensis

<400> SEQUENCE: 1

```
acgctgtaaa cgatgagtgc taaatgtgag gattttatct ttgtattgta gctaacgcgt    60
taagcactcc gcctccccac tcaggtcgca agactaaaac tcaaaggaat tgacggggac   120
ccgcacaagg ctggagcatg tggtttaatt cgatgcaacg cgaaaaacct taccactttt   180
tgacatgaag gtcgtatccc tcctaatagg gggagtcagt tcggctggac cttacacagg   240
tgctgcatgg ctgtcgtcag ctcgtgtcgt gagatgttgg gttaagtccc gcaacgagcg   300
caaccctcat ccttagttac aacaggtaa tgctgggcac tctaaggaaa ctgccagtga    360
taaactggag gaaggtgggg atgatgtcaa gtcagcacgg cccttataag gtgggctaca   420
cacgtgctac aatggcaact acaataggtc gcgagaccgc aaggtttagc taatccataa   480
aagttgtctc agttcggatt gttctctgca actcgagagc atgaagtcgg aatcgctagt   540
aatcgtggat catcatgcca cggtgaatac gttctcgggt cttgtacaca ctgcccgtca   600
cgccatggga attggcttaa ctcgaagctg gtgtgctaac cgcaaggaag cagccattta   660
aggttgggtt agtgactagg gtg                                          683
```

<210> SEQ ID NO 2
<211> LENGTH: 683
<212> TYPE: DNA
<213> ORGANISM: E. Canis

<400> SEQUENCE: 2

```
acgctgtaaa cgatgagtgc taaatgtgag gattttatct ttgtattgta gctaacgcgt    60
taagcactcc gcctccccac tcaggtcgca agactaaaac tcaaaggaat tgacggggac   120
ccgcacaagg ctggagcatg tggtttaatt cgatgctacg cgaaaaacct taccactttt   180
tgacatgaag gtcgtatccc tcctaacagg gggagtcagt tcggctggac cttacacagg   240
tgctgcatgg ttgtcgtcag ctcgtgtcgt gagatgttgg gttaagtccc gcaacgagcg   300
caaccctcat tcttagttac aacaggtaa tgctgggcac tctaaggaaa ctgccagtga    360
taaactggag gaaggtcccc atgatgtcaa atcagcacgg cccttatagg gtgggctaca   420
cacgtgctac aatggcaact acaataggtt gcgagaccgc aaggtttagc taatccataa   480
aagttgtctc agttcggatt gttctctgaa actcgagagc atgaagtcgg aatcgctagt   540
aatcgtggat catcacgcca cggtgaatac gttctcgggt cttgtacaca ctgcccgtca   600
cgccatggga attggcttaa ctcgaagctg gtgtgctaac cgcaaggaag cagccattta   660
aggttgggtt agtgactagg gtg                                          683
```

<210> SEQ ID NO 3
<211> LENGTH: 29
<212> TYPE: DNA
<213> ORGANISM: Artificial Sequence
<220> FEATURE:
<223> OTHER INFORMATION: The artificial sequence comprises an
      oligonucleotide primer complementary to E.
      chaffeensis DNA.

<400> SEQUENCE: 3

```
caattgctta taaccttttg gttataaat                                29
```

<210> SEQ ID NO 4
<211> LENGTH: 27
<212> TYPE: DNA
<213> ORGANISM: Artificial Sequence
<220> FEATURE:
<223> OTHER INFORMATION: The artificial sequence comprises an
     oligonucleotide primer complementary to E.
     chaffeensis DNA.

<400> SEQUENCE: 4

```
tataggtacc gtcattatct tccctat                                  27
```

<210> SEQ ID NO 5
<211> LENGTH: 31
<212> TYPE: DNA
<213> ORGANISM: Artificial Sequence
<220> FEATURE:
<223> OTHER INFORMATION: The artificial sequence comprises an
     oligonucleotide primer  complementary to the genus
     Ehrlichia.

<400> SEQUENCE: 5

```
gccattagaa atgatgggta atactgtata a                             31
```